US006653277B1

(12) United States Patent
Golz-Berner et al.

(10) Patent No.: US 6,653,277 B1
(45) Date of Patent: Nov. 25, 2003

(54) PERFUME COMPOSITIONS WITH A SCENT SEQUENCE

(75) Inventors: Karin Golz-Berner, Monaco (MC); Leonhard Zastrow, Monaco (MC)

(73) Assignee: Coty B.V. (NL)

( * ) Notice: Subject to any disclaimer, the term of this patent is extended or adjusted under 35 U.S.C. 154(b) by 0 days.

(21) Appl. No.: 09/980,331

(22) PCT Filed: May 26, 2000

(86) PCT No.: PCT/DE00/01783

§ 371 (c)(1),
(2), (4) Date: Nov. 30, 2001

(87) PCT Pub. No.: WO00/72804

PCT Pub. Date: Dec. 7, 2000

(30) Foreign Application Priority Data

May 31, 1999 (DE) .......................................... 19925971

(51) Int. Cl.$^7$ ................................................. A61K 7/46
(52) U.S. Cl. ........................................... 512/4; 510/101
(58) Field of Search ............................. 510/101; 512/4

(56) References Cited

U.S. PATENT DOCUMENTS 5,508,259 A * 4/1996 Holzner et al. ................ 512/4
6,390,453 B1 * 5/2002 Frederickson et al. ........ 261/26

FOREIGN PATENT DOCUMENTS

EP          714709 A1 *  6/1996

* cited by examiner

*Primary Examiner*—John Hardee
(74) *Attorney, Agent, or Firm*—Pendorf & Cutliff

(57) ABSTRACT

The invention relates to perfume compositions, wherein different scent notes are successively released (scent sequence). According to the invention, the perfume composition comprises at least a first perfume ingredient consisting of at least a first and a second aromatic substance in the absence of alcohol, wherein the aromatic substances are contained in microcapsules, at least a second perfume composition consisting of at least a third and a fourth aromatic substance in the absence of alcohol, wherein the aromatic substances are contained in microcapsules, and a cosmetic gel in which the first and the second perfume compositions are distributed.

5 Claims, No Drawings

PERFUME COMPOSITIONS WITH A SCENT SEQUENCE

BACKGROUND OF THE INVENTION

1. Field of the Invention

The invention relates to perfume compositions, wherein different scent notes are successively released (scent sequence).

2. Description of the Related Art

It is known that perfume preparations with differing volatilities after opening a perfume flask release a so-called head note followed by a heart note and finally a fond note. Generally, the head note is determined by low boiling alcohols such as ethanol, while an extended fond note can be accomplished, for example, by less volatile oils or bonding to a carrier with the assistance of high boiling solvents.

In order to influence the volatility of perfume compositions and to achieve an effectiveness period being as long as possible on the skin of the user, among other methods the enclosure of perfumes in capsules has been applied. For example, EP 838216 suggests an encapsulation using high-bloom gelatine capsules wherein the aromatic substance is provided encapsulated together with a volatile solvent and a non-volatile co-solvent. Further, known perfume compositions comprise cyclodextrines (e.g. from EP 0013688) or cyclodextrines in an aqueous carrier, moisture-keeping agents and agents active on the surface (e.g. from WO 98/56341).

SUMMARY OF THE INVENTION

It is an object of the invention to provide a perfume composition wherein, when applied onto the skin, different scent notes are released successively but nearly completely isolated from each other.

According to the invention, the perfume composition comprises
a) at least a first perfume ingredient consisting of at least a first and a second aromatic substance in the absence of alcohol, wherein the aromatic substances are contained in microcapsules, and
b) at least a second perfume ingredient consisting of at least a third and a fourth aromatic substance in the absence of alcohol, wherein the aromatic substances are contained in microcapsules, and
c) a cosmetic gel in which the first and the second perfume ingredients are distributed.

In an advantageous embodiment of the invention, the microcapsules of the first perfume ingredient or the second perfume ingredient contain, apart from the aromatic substances, lamellar liquid crystals or mixtures of liquid crystals.

The microcapsules are manufactured using common methods, wherein a liquid is used as a suspension medium for the microcapsules and wherein the emulsification/dispersion of two or more phases non-miscible with each other is performed. These methods include interfacial polymerisation, in-situ polymerisation, solvent evaporation, gelatinisation, pressure extrusion, polymer-polymer incompatibility, and simple and complex coacervation. The three last methods are preferred.

During coacervation, the individual droplets of the wall polymer settle on the surfaces of a core material, wherein it is essential that the core is insoluble in the solvent of the polymer material, and the wall polymer is hardly able to distribute in the core material. After completely covering the surface of the core material with microdroplets followed by coalescence the coacervates form a wall around the core material. If necessary, this wall may be hardened in addition. (for coacervation, see for instance Hallcrest, Handbook of Thermochrome Liquid Crystal Technology (1991), pp. 11–12).

If liquid crystals are selected as core material, the process described above may also be performed in such a manner that the lamellar liquid crystals are brought into contact with the respective aromatic substances and are transformed into coacervates. Different wall thicknesses can be accomplished using known methods.

The capsules formed may have a diameter ranging from 5–10 µm up to 2000 µm. In case of diameters below 500 µm, the wall thicknesses range from 5 to 20 µm.

DETAILED DESCRIPTION OF THE INVENTION

In a preferred embodiment the wall thicknesses of the micro-capsules range from 100 to 2000 nm.

In a further preferred embodiment three different perfume ingredients are encapsulated in the microcapsules. The first perfume ingredient comprises two orange scent substances, the second perfume ingredient two vanilla scent substances, and the third perfume ingredient two rose scent substances.

Usable liquid crystals include cholesteric substances such as cholesterol, cholesterol ester, phytosterols, particularly B-sitosterol and camposterol, phytosterol ester, dihydrosterol ester, non-specific sterol derivatives or else mixtures of cholesterol with 2-acetaminoalkane-1,3-diolene and 2-acylami-noalkane-1,3-diolen as well as chiralically nematic substances such as (2-methyl butyl)phenyl-4-alkyl(oxy) benzoate.

Examples of aromatic substances in the perfume compositions according to the invention include: ambre, anekole $C_{10}H_{12}O$, angelica root oil, artemisia oil, basil oil, rose oil, lavender oil, bay oil, benzaldehyde $C_7H_6O$, bergamot oil, benzyl acetate $C_9H_{10}O_2$, camphor $C_{10}H_{17}O$, calamus oil, carrot oil, camomile oil, citronella oil, couramine $C_9H_6O_2$, cyprene oil, dihydromyrcenol $C_{10}H_{20}O$, jasmine, mimosa, muscone $C_{16}H_{30}O$, narcissus, orange oil, rose oxide $C_{10}H_{18}O$, sandelwood oil, vanilla $C_8H_8O_3$. A wide variety of other aromatic substances can be used, in particular variants of individual aromatic substances having similar scent nuances.

It is an essential characteristic of the invention that at least two aromatic substances form each one of several perfume ingredients within the perfume composition according to the invention and that no light volatile solvent, i.e. no alcohol, is added to these perfume ingredients.

Preferably, the first, second, third and fourth aromatic sub-stances have a different volatility, i.e. a different boiling point.

It is further preferable that the volatility increases from the first to the fourth and, if applicable, any further aromatic substance.

In another embodiment of the invention, the wall thickness of the microcapsules differs among the individual perfume ingredients and preferably increases from the first perfume ingredient to the second perfume ingredient and, if applicable, to any further perfume ingredient. This allows the capsule walls of the microcapsules to break open at different points in time.

For example, the wall thickness of the capsules containing the first perfume ingredient may be 100 to 200 nm, that of the capsules containing the second perfume ingredient 400 to 500 nm and that of the capsules containing the third perfume ingredient may exceed 500 nm.

The invention allows to apply onto the skin different scent notes consisting of at least two different aromatic substances in a micro-encapsulated form, to destroy during the soft initial application of the gel onto the skin the capsule walls of the capsules containing a first perfume ingredient and thus to release the mixture of the first and second aromatic substances as the "head note" of the perfume.

A little later, a second scent note is released in the form of the mixture of the at least third and fourth aromatic substances with no essential mixed scent phase occurring between both aromatic substances.

If applicable, a third or further scent note is released in the form of a mixture of at least a fifth and a sixth and, if applicable, further aromatic substances (mixtures), each with no essential mixed scent phase occurring in between.

Hitherto it is unclear what causes the release of the further aromatic substances without any visible external influence and what prevents the occurrence of a mixed scent phase. It can be assumed that there is an interaction with skin proteins plus the influence of skin temperature.

In the sense of this invention, "without an essential mixed scent phase" means that a mixture of two scent notes is nearly imperceptible and, if at all, occurs for a few seconds only (e.g. 2–8 seconds).

The combination according to the invention creates a scent sequence desired by the user which up to now could not be created in this form. Although it was possible in the prior art to create a scent sequence using the adherence to the skin and different solvents with varying boiling points plus, if applicable, further additives, but firstly this always required the presence of solvents such as alcohols, and secondly, always an extended and hardly influenceable mixed scent phase occurred during which no clear scent note could be discerned.

Further, the use of liquid crystals having a lamellar phase according to the invention allows a longer binding of the aromatic substances to said phase and as a whole a delayed release of the scents.

Moreover, temperature-sensitive and thermochrome liquid crystals allow especially attractive colour effects shown by the microcapsules in the gel. This factor may be further enhanced by adjusting the viscosity degree of the gel to a higher level, e.g. above 50000 Pa·s by depositing the various microcapsules punctually, helically, on discrete locations in the gel, in layers or in another distribution and keeping them at these locations. A uniform distribution may also be accomplished by intensive shaking or by distributing the microcapsules in a less viscous gel.

A preferred perfume composition according to the invention includes three perfume ingredients. The first perfume ingredient comprises two different orange scent substances, the second perfume ingredient two different vanilla scent substances, and the third perfume ingredient two different rose scent substances.

As mentioned above, a preferred embodiment of the invention includes the selection of the wall thickness of the microcapsules and the volatility of the aromatic substances in such a way that after applying the perfume composition onto the skin the aromatic substances of the first perfume ingredient are released first, followed—without an essential mixed scent phase—by the aromatic substances of the second perfume ingredient, followed by the aromatic substances of the third and, if applicable, any further perfume ingredients.

The dispersion of the perfume ingredients may be carried out in known cosmetic gels. These include carbomer, xanthane rubber, carrageenan, acacia gum, guar gum, agar-agar, alginates and tyloses, carboxymethyl cellulose, hydroxyethyl cellulose, certain polyacrylates, polyvinyl alcohol, polyvinyl pyrrolidone, silicone gels.

Now the invention will be described by way of examples. All percentage figures designate weight percent unless specified otherwise.

EXAMPLE 1

Liquid crystals of the cholesteryl 2,4 dichloro benzoate, cholesteryl oleyl carbonate, cholesteryl nonanoate and cholesteryl chloride types were brought into contact with a first mixture of aromatic substances comprising two different orange scent substances (scent liquid 1) having a concentration of 8 wt % in a perfume oil and transformed in the common manner into a coacervate. The wall thickness of the microcapsules formed was approximately 120 to 150 nm.

Then, the liquid crystals cholesteryl oleyl carbonate, cholesteryl nonanoate and cholesteryl chloride were brought into contact with a second mixture of aromatic substances comprising two different vanilla scent substances (scent liquid 2) having a concentration of 8 wt % in oil and transformed in the common manner into a coacervate. The wall thickness of the microcapsules formed was approximately 300 to 450 nm.

Then, the liquid crystals cholesteryl oleyl carbonate, cholesteryl nonanoate and cholesteryl chloride were brought into contact with a third mixture of aromatic substances comprising two different rose scent substances (scent liquid 3) having a concentration of 8 wt % in perfume oil and transformed in the common manner into a coacervate. The wall thickness of the microcapsules formed was approximately >500 nm.

The three aromatic substances were dispersed in a silicone gel successively and by cautious distribution or by injecting at a temperature ranging from 15 to 45° C. resulting in the following composition (in wt %):

| | |
|---|---|
| silicone powder | 3 |
| silicone oil | to make 100 |
| scent liquid 1 | 2 |
| scent liquid 2 | 2 |
| scent liquid 3 | 2 |

The individual droplets of the perfume composition were clearly discernible by colour differences and thus provided an additional attractive optical effect.

What is claimed is:

1. Perfume composition with a scent sequence, comprising
   a) at least a first perfume ingredient consisting of at least a first and a second aromatic substance in the absence of alcohol, wherein the aromatic substances are contained in microcapsules, and
   b) at least a second perfume ingredient consisting of at least a third and a fourth aromatic substance in the absence of alcohol, wherein the aromatic substances are contained in microcapsules, and
   c) a cosmetic gel in which the first and the second perfume ingredients are distributed,
   where the microcapsules are formed by emulsion or dispersion from a liquid suspension medium and at least one phase which is snot miscible with the suspension medium,
   said microcapsules have a wall thickness which increases from the first perfume ingredient to the second perfume ingredient and, if applicable, to any further perfume ingredient, and
   wherein the first, second, third and fourth aromatic substances have different volatilities which increases from the first to the fourth and, if applicable, any further aromatic substance.

2. Perfume composition according to claim 1, wherein the microcapsules of the first perfume ingredient or the second perfume ingredient or both contain, apart from the aromatic substances, lamellar liquid crystals or liquid crystal mixtures.

3. Perfume composition according to claim 1, wherein the wall thicknesses of the microcapsules range from 100 to 2000 nm.

4. Perfume composition according to claim 1, comprising three different perfume ingredients, wherein the first perfume ingredient comprises two orange scent substances, the second perfume ingredient two vanilla scent substances, and the third perfume ingredient two rose scent substances.

5. Perfume composition according to claim 1, wherein the microcapsules and the aromatic substances are selected so that, after applying the perfume composition onto the skin, at first the aromatic substances of the first perfume ingredient are released and at a later time, without an essential mixed scent phase, the aromatic substances of the second perfume ingredient are released.

\* \* \* \* \*